United States Patent [19]
Koca et al.

[11] Patent Number: 5,879,880
[45] Date of Patent: Mar. 9, 1999

[54] METHOD OF DIAGNOSING BY DETERMINING FORMIC ACID TO NICOTINIC ACID RATIO

[75] Inventors: Jaroslav Koca, Brno, Czech Rep.; Yveta Germano, Elmsford, N.Y.; Vaclav Racansky, Brno, Czech Rep.

[73] Assignee: Peregrine Pharmaceuticals, Inc., Gainesville, Ga.

[21] Appl. No.: 842,941

[22] Filed: Apr. 25, 1997

Related U.S. Application Data

[60] Provisional application No. 60/016,656 Apr. 30, 1996.

[51] Int. Cl.⁶ ..................................................... C12Q 1/00

[52] U.S. Cl. ................................. 435/4; 436/64; 436/813

[58] Field of Search ......................... 435/4, 7.23; 436/63, 436/64, 811, 813

[56] References Cited

U.S. PATENT DOCUMENTS

| | | | |
|---|---|---|---|
| 4,542,750 | 9/1985 | Ettare | 128/760 |
| 4,705,756 | 11/1987 | Spillert et al. | 436/64 |
| 5,430,049 | 7/1995 | Gaut | 514/410 |
| 5,508,201 | 4/1996 | Brandt et al. | 436/64 |

OTHER PUBLICATIONS

Tamulevicius P., N—methylnicotinamide as a Possible Prognostic Indicator of Recovery From Leukaemia in Patients Treated with Total–Body Irradiation and Bone Marrow Transplants, Strahlentherapie 160(4):249–254, Jun. 1984.

*Primary Examiner*—Ralph Gitomer
*Attorney, Agent, or Firm*—Bruce F. Jacobs

[57] ABSTRACT

A method for determining whether a mammal should be medically investigated for a cancerous or pre-cancerous condition based upon the formic acid to nicotinic acid ratio in the blood of the mammal.

14 Claims, No Drawings

METHOD OF DIAGNOSING BY DETERMINING FORMIC ACID TO NICOTINIC ACID RATIO

This application is from Provisional Application 60/016,656 filed Apr. 30, 1996.

FIELD OF THE INVENTION

This invention relates to the field of cancer diagnostics.

BACKGROUND OF THE INVENTION

Cancer is often a deadly disease. In the United States, for instance, cancer is the second leading cause of death after heart disease and accounts for about 526,000 deaths annually. One of three Americans develops cancer and one of four Americans dies of cancer. The number of deaths attributed to cancer is rising, because of a combination of a growing elderly population and a decline in deaths from heart disease.

Cancer may be detected in several ways. In a biopsy, for instance, tissue suspected of being cancerous is removed and tested for malignancy. For routine screening purposes, however, biopsies are undesirable, because (i) the cancer has to have progressed sufficiently so that a tissue sample is available, and (ii) the tests and equipment to conduct the biopsies are expensive and time-consuming. Moreover, biopsies may metastatically spread the cancer through blood and/or tissue droplets. There is a need to develop a cancer detection screening test which is effective, inexpensive, and easily performed.

It has now been unexpectedly discovered that the levels of certain acids in a mammal change when the mammal has developed a cancerous condition or a pre-cancerous condition.

As used in this application, a "cancerous condition" is a condition in which a mammal's immune system has failed to recognize and destroy malignant cells. A "pre-cancerous condition" is a condition which has been reported as potentially developing into a cancerous condition.

It is an object of this invention to develop a method for determining whether a mammal should be medically investigated for a cancerous condition.

It is a further object of this invention to develop a method that determines whether a mammal should be medically investigated for a pre-cancerous condition.

It is a further object of this invention to develop a simple, relatively inexpensive screening technique which can be easily performed and is likely to identify early stages of a cancer's development.

It is a further object of this invention to develop a non-invasive cancer detection method that does not carry the risk of metastatic spread of cancer via blood and/or tissue droplets.

These and still further objects will be apparent from the following description of this invention.

SUMMARY OF THE INVENTION

The present invention is directed to a method for determining whether a mammal should be medically investigated for a cancerous condition or a pre-cancerous condition by performing the steps of (i) obtaining a sample of blood from a mammal; (ii) measuring the amount of formic acid in the sample, (iii) measuring the amount of nicotinic acid in the sample, and (iv) calculating the formic acid to nicotinic acid ratio of the sample, and (v) determining whether the formic acid to nicotinic acid ratio is sufficiently high to warrant medical investigation. Generally, a formic acid to nicotinic acid ratio that is more than about 2.7 indicates the mammal has a sufficiently high probability of having a cancerous or a pre-cancerous condition to warrant medical investigation.

DESCRIPTION OF PREFERRED EMBODIMENTS

The amount of formic acid or nicotinic acid in a mammal may be measured by any suitable means. Preferably, the acids are measured by drawing blood and by conducting appropriate blood tests in an analyzer. Suitable analyzers will generally utilize species separation techniques, e.g. capillary electrophoresis, capillary isotachophoresis and capillary chromatography analyzers. Examples of such analyzers include the CS isotachophoteric analyzer EA 100, available from VILLA-LABECO, Slovak Republic, and the Hewlett Packard[3D] Capillary Electrophoresis. Other functionally equivalent analyzers may be used.

The amounts of formic acid and nicotinic acid will preferably be measured from hemolyzed blood (as opposed to whole blood) since it has been determined that hemolyzed blood produces results that are more accurate than whole blood. The amount of acid is preferably measured on a per hemoglobin basis when a mammal has anemia. The amount of formic acid and nicotinic acid of a mammal may be measured by calibrating an analyzer, preparing a hemolysate, introducing the hemolysate into the analyzer, and determining the acid content in the hemolysate.

To calibrate the analyzer, a known amount of acid (nicotinic or formic acid) is added to a standard solution and the solution is placed in the analyzer. The analyzer (having appropriate electrolytes suitable for detecting the nicotinic acid) assigns a peak to each component of the standard solution within a specific time after the solution is introduced into the analyzer. The peak corresponding to the acid can be readily determined by comparing the peaks generated by the standard solution with the peaks generated by a solution without the known amount of acid. When a blood sample is later run through the analyzer, the amount of the acid can be determined by the area under the peak corresponding to the acid.

To prepare a suitable hemolysate for formic acid detection, a blood sample drawn from a mammal is subjected to hemolysis and a hemolysate is produced. For instance, venous (or arterial) blood is drawn from a mammal, collected into preferably heparinized tubes and centrifuged until the blood separates into plasma and sedimented blood cells. The sedimented blood cells may then be washed with a saline solution, centrifuged with the saline mixture for several minutes, and the resulting supernatant may then be discarded. The sedimented cells are then lysed to form a hemolysate by adding distilled water to the cells or by any other such means. To determine the amount of formic acid in the hemolysate, it is preferably introduced into a calibrated analyzer as discussed above.

To prepare the hemolysate for nicotinic acid detection, the above procedure for formic acid is used. Thereafter, the hemolysate is preferably deproteinized, e.g. by the addition of acetone-water, before it is introduced into an analyzer. Deproteinization is preferred since it removes proteins from the blood which may affect the accuracy of some measuring techniques, particularly analyzers that use electrophoresis or chromatography techniques.

Once the amounts of formic and nicotinic acids in the hemolysates have been determined, the formic acid to nicotinic acid ratio is obtained by dividing the measured amounts of formic acid and nicotinic acid. Generally, a formic acid to nicotinic acid ratio of at least 2.2, preferably at least 2.5, and even more preferably at least 2.7, is indicative of the mammal having a sufficiently high probability of having a cancerous or a pre-cancerous condition to warrant further medical investigation. Correspondingly, a formic acid to nicotinic acid ratio that is less than 2.2, more preferably less than 2.0, and even more preferably less than 1.8, indicates the mammal has a sufficiently low probability of having a cancerous or a pre-cancerous condition that additional medical investigation is not warranted.

The ratio of a mammal may vary depending upon factors such as (i) the method used to measure the amounts of nicotinic and formic acids, (ii) medications in the system of the mammal, (iii) the length of time since the most recent chemotherapy and/or radiation therapy treatment, (iv) the mammal's general fatigue and/or stress level, and (v) the overall state of the mammal's immune system. These factors may need to be considered when drawing firm conclusions based upon the cancer diagnostic of the present invention, especially when the ratio is in the range of about 1.8 to 2.7.

Cancerous conditions for which the method of the present invention has been found to indicate that further medical investigation is warranted include carcinomas, sarcomas, myelomas, lymphomas, and leukemias. More specifically, adenocarcinoma of the larynx, adenocarcinoma of the nasopharynx, bladder carcinoma, brain cancer, breast adenocarcinoma, cancer of the connective tissue, cancer of the parotid gland, cancer of the trachea, carcinoma digestive tract, colon adenocarcinoma, gall bladder adecarcinoma, Hodgkin's disease, kidney adenocarcinoma, liver and bile duct adenocarcinoma, lung adenocarcinoma, lung small cell carcinoma, malignant melanoma, metastacized breast adenocarcinoma, rectal adenocarcinoma, prostate adenocarcinoma, rectosigmoidal adenocarcinoma, sarcoma, skin cancer, stomach adenocarcinoma, testicular cancer, rectal adenocarcinoma, Kaposi's sarcoma, lymphoma, leukemia, and multiple myeloma. Other cancerous conditions are expected to be within the scope of this invention.

Cancerous or pre-cancerous conditions for which the method of the present invention has been found to indicate that further medical investigation is warranted include, elevated PSA counts, elevated markers including but not limited to CEA, CA-125, CA-15, βHCG, elevated liver enzymes, neoplasia, dysplasia, and conditions that lower the immune system's ability to fight malignancies. Other conditions that are not currently recognized as pre-cancerous conditions by conventional teachings but which may possibly lead to medically-recognized pre-cancerous conditions include significantly depressed immune system, increased levels of immunoglobulins, chronic bacterial lung infection, chronic inflammation of the uterus, and other chronic infections and/or inflammations. Other pre-cancerous conditions are within the scope of this invention.

Since the present invention can be repeated frequently (due to its simplicity and relative low cost), the invention can be used as a general screening technique before conventional and more invasive cancer diagnostic tests are ordinarily used, i.e. during blood work at periodic checkups. If the present invention indicates a mammal should be medically investigated for a cancerous or a pre-cancerous condition, conventional riskier (and more expensive) intrusive techniques may then be used to identify the specific condition. Accordingly, by use of the present invention cancer treatment may begin earlier than it would have otherwise have begun. Alternatively, the present invention may be used to monitor the progress of a pre-cancerous condition that has been previously identified, or to monitor the recurrence of a cancerous condition which has been previously treated.

The reason relatively higher formic acid to nicotinic acid ratios indicate a sufficiently high probability of having a cancerous or a pre-cancerous condition to warrant medical investigation has not been conclusively determined and the Applicant will not be bound by theory. It is believed, however, that increased formic acid in a mammal is destructive and may cause cancer or that reduced nicotinic acid in a mammal may inhibit a mammal's capacity to fight malignancies. In either case, a higher ratio results.

The following non-limiting examples illustrate the present invention.

EXAMPLE 1

The formic acid:nicotinic acid ratio of a mammal on a per hemoglobin basis was determined as follows. To calibrate a CS isotachophoteric analyzer EA 100 to detect formic acid, a standard mixture of blood containing a known amount of formic acid was placed in the analyzer. The analyzer then separated the blood into its separate components and assigned the formic acid a peak within a specific time after being introduced into the analyzer. The formic acid peak was observed. The separation column consisted of a pre-separation capillary (9 cm×0.8 mm I.D.) and a main capillary (16 cm×0.3 mm I.D.). Both capillaries were joined with a conductivity detector. Additionally, the main capillary was equipped with UVD-2 on-column photometric detector which was set at 254 nm.

The calibration and peak identification were done using a method of internal standard (10 µl of formic acid at the concentration of 1 mM was added directly to the sample). For data collection, data analysis and system control, firm EA-Analyst software was used.

The optimal electrolyte conditions for detecting the acid are indicated in Table 1.

TABLE 1

| Leading Electrolyte | 10 mM HCl + β-alanin, pH 3.0 + 0.1% polyethylene glycol |
| --- | --- |
| Terminating Electrolyte | 5 mM propionic acid |
| Sample | 20 µl of hemolysate |
| Operational current: | |
| Pre-separation capillary | 350 µA |
| Separation capillary | 45 µA |

To prepare a hemolysate for the detection of formic acid, venous blood was collected from the mammal into heparinized tubes (vacutainer, sodium heparin tubes) and the blood was centrifuged until the plasma and cellular components separated. The sedimented blood cells were then washed with a saline solution, i.e. isotonic saline solution (0.9% NaCl). The resulting saline mixture was centrifuged for 3 minutes, the supernatant discarded, and the cells were lysed to form the hemolysate by adding distilled water to the washed cells. To measure the amount of formic acid, the hemolysate was then placed into the analyzer and the acid content was evaluated.

To measure the nicotinic acid, a Hewlett Packard$^{3D}$ CE system analyzer (a free solution capillary zone electrophoresis analyzer) was calibrated according to the procedure described above, except that the analyzer was calibrated to detect nicotinic acid. The analyzer had a fuces-silica capillary 600 mm×50 µm I.D. (extended light path). An on-column diode array detector (190–600 nm)(515 mm from an end of the capillary) was used in all measurements. Peak calibration was accomplished by comparing both electrophoretic mobilities and UV spectra with those of authentic standards of nicotinic acid and 2-chloronicotinic acid.

To obtain optimal electrolyte conditions, 0.1M Boric acid (pH 8.5) buffered solution was used as a working electrolyte. All samples and the buffers were filtered through a sterilizing 0.2 µm filter. Moreover, the buffers were degassed by ultrasound for at least 10 minutes before use to avoid microbubbles (which could interfere with the accuracy of the peak detection). All solutions were prepared with Milli Q deionized water. The capillary was preconditioned for 10 minutes with 0.1 NaOH and 15 minutes with background electrolyte before the first run and then for 1 minute with 0.1M NaOH for 1 min with deionized water and for 3 minutes with background electrolyte prior to each following run.

To prepare a hemolysate for the detection of nicotinic acid, the procedure above was first repeated. Then, 0.5 ml of the hemolysate was pipeted into an Eppendorf tube and 1 ml of acetone-water (20 µl of 5 mM solution) was added to deproteinize the hemolyzate. The mixture was then centrifuged at 5,000 g (g being a unit of centrifuge overload) for 10 minutes, and 1 ml of supernate was transferred into a microtube containing 0.5 ml chloroform to clean unwanted materials. The mixture was then shaken and centrifuged at 5,000 g for 3 minutes. 0.5 ml of aqueous layer dried at 60° C. 200 µl of methanol were added to the residue, and the solvent was removed by drying. A residue formed which was dissolved in water and injected into the analyzer.

The formic acid to nicotinic acid ratio was then obtained by dividing the measured amount of nicotinic acid by the measured amount of formic acid.

EXAMPLE 2

The procedure of Example 1 was repeated except that the procedure was administered to 63 volunteers. None of the volunteers had ever been treated for cancer.

Volunteers 1–5, 7–23, 25–26, 28–30, 32–38 had formic acid to nicotinic acid ratios that were about 2.2 or greater, which indicated that there was a high probability that the volunteers had a cancerous or a pre-cancerous condition to warrant further medical investigation. Volunteers 6, 24, 27, 31, 39–59, and 61 had formic acid to nicotinic acid ratios lower than 2.2 which indicated that the volunteers were not likely to not have a cancerous or pre-cancerous condition.

To verify the results obtained using the procedure of Example 1, the volunteers were examined for health problems by conventional techniques, e.g. X-rays, CT scans, MRI, sonograms, biopsies, blood tests evaluating various markers including but not limited to PSA, CEA makers, immune system indicators including but not limited to immunoglobulins, various antigens, interleukins, lymphocytes. An independent diagnosis was determined for each individual. Table 2 identifies the ratios and results of the volunteers who were independently diagnosed with cancer. Table 3 identifies the ratios and results of the volunteers who were independently diagnosed as not having cancer.

89% of the volunteers independently diagnosed as having a cancerous or a pre-cancerous condition had a formic acid to nicotinic acid ratio greater than 2.2 indicating that the method of the present invention was an effective cancer-diagnostic. Volunteers 6, 24, 27, 31 (having formic acid to nicotinic acid ratios that were less than about 2.2) were independently diagnosed as having a cancerous or a pre-cancerous condition. The discrepancy between results could have been attributed between statistical error or an inaccurate independent diagnosis.

Volunteers 60 and 62, independently diagnosed as healthy (having formic acid to nicotinic acid ratios more than 2.2) had family histories of malignancies and chronic infections and could have been experiencing pre-cancerous conditions that were not currently detectable by conventional diagnostic methods. Volunteer 63 (having a formic acid to nicotinic acid ratio more than 2.2) had been undergoing severe emotional trauma and it is possible that such prolonged stress was depressing the immune system of the individual.

TABLE 2

| VOLUNTEER | FORMIC ACID: NICOTINIC ACID | INDEPENDENT DIAGNOSIS |
|---|---|---|
| 1 | 6.84 | Prostate Adenocarcinoma |
| 2 | 2.62 | Malignant Melanoma |
| 3 | 12.22 | Breast Adenocarcinoma |
| 4 | 5.47 | Rectal Adenocarcinoma |
| 5 | 22.69 | Testicular Cancer |
| 6 | 1.24 | Brain Cancer |
| 7 | 6.10 | Colon Adenocarcinoma |
| 8 | 4.09 | Kidney Adenocarcinoma |
| 9 | 2.55 | Testicular Cancer |
| 10 | 2.78 | Sarcoma |
| 11 | 6.98 | Testicular Cancer |
| 12 | 3.96 | Hodgkin's Disease |
| 13 | 2.80 | Testicular Cancer |
| 14 | 7.35 | Adenocarcinoma of the Larynx |
| 15 | 18.57 | Lung Adenocarcinoma |
| 16 | 2.68 | Intestinal Adenocarcinoma |
| 17 | 8.37 | Malignant Melanoma |
| 18 | 2.93 | Skin Carcinoma |
| 19 | 3.80 | Testicular Cancer |
| 20 | 12.52 | Lung Adenocarcinoma |
| 21 | 12.68 | Gall-Bladder Adenocarcinoma |
| 22 | 22.78 | Colon Adenocarcinoma |
| 23 | 3.06 | Testicular Cancer |
| 24 | 1.35 | Cancer of the Parotid Gland |
| 25 | 2.82 | Malignant Melanoma |
| 26 | 7.74 | Testicular Cancer |
| 27 | 1.57 | Malignant Melanoma |
| 28 | 13.66 | Bladder Carcinoma |
| 29 | 14.55 | Testicular Cancer |
| 30 | 5.40 | Stomach Adenocarcinoma |
| 31 | 1.23 | Prostate Adenocarcinoma |
| 32 | 4.88 | Cancer of the Connective Tissue |
| 33 | 11.49 | Kidney Adenocarcinoma |
| 34 | 14.45 | Testicular Cancer |
| 35 | 66.88 | Rectal Adenocarcinoma |
| 36 | 12.11 | Prostrate Adenocarcinoma |
| 37 | 25.32 | Lung Adenocarcinoma |
| 38 | 4.11 | Bladder Carcinoma |

TABLE 3

| VOLUNTEER | FORMIC ACID: NICOTINIC ACID | INDEPENDENT DIAGNOSIS |
|---|---|---|
| 39 | 1.65 | Healthy |
| 40 | 1.05 | Healthy |
| 41 | 1.96 | Healthy |
| 42 | 2.09 | Healthy |
| 43 | 1.43 | Healthy |
| 44 | 1.97 | Healthy |
| 45 | 1.72 | Healthy |
| 46 | 2.13 | Healthy |
| 47 | 1.44 | Healthy |
| 48 | 2.00 | Healthy |
| 49 | 1.33 | Healthy |
| 50 | 1.65 | Healthy |

TABLE 3-continued

| VOLUNTEER | FORMIC ACID: NICOTINIC ACID | INDEPENDENT DIAGNOSIS |
|---|---|---|
| 51 | 1.98 | Healthy |
| 52 | 2.16 | Healthy |
| 53 | 2.05 | Healthy |
| 54 | 1.76 | Healthy |
| 55 | 2.04 | Healthy |
| 56 | 1.65 | Healthy |
| 57 | 2.11 | Healthy |
| 58 | 1.04 | Healthy |
| 59 | 2.01 | Healthy |
| 60 | 15.03 | Healthy |
| 61 | 2.10 | Healthy |
| 62 | 6.03 | Healthy |
| 63 | 3.52 | Healthy |

EXAMPLE 3

To monitor the progress and/or recurrence of cancerous conditions that had been treated within the last six months, the procedure of Example 1 was repeated except that the invention was administered to additional volunteers numbered 64–105. All of the volunteers were independently diagnosed as having cancer after treatment.

91% of the volunteers independently verified as having cancer had a formic acid to nicotinic acid ratios greater than about 2.2, (likely to have a cancerous or a pre-cancerous condition). Volunteers 68, 69, 92 and 94 had formic acid to nicotinic acid ratios that were below 2.2. The discrepancy between these results and the independent diagnoses could have been due to recent cancer treatments and/or statistical error.

Table 4 shows the volunteers who were independently diagnosed as having cancer with corresponding formic acid to nicotinic acid ratios.

TABLE 4

| VOLUN-TEER | FORMIC ACID: NICO-TINIC ACID | INDEPENDENT DIAGNOSIS | PRIOR TREATMENT |
|---|---|---|---|
| 64 | 5.39 | Colon adenocarcinoma | Chemotherapy |
| 65 | 5.07 | Rectos igmoidal adenocarcinoma | Chemotherapy |
| 66 | 12.09 | Lung adenocarcinoma | Radiation, Chemotherapy |
| 67 | 5.16 | Malignant melanoma | Surgery Chemotherapy (2nd series) |
| 68 | 0.40 | Testicular cancer | |
| 69 | 0.14 | Testicular cancer | Chemotherapy (2nd series) |
| 70 | 5.32 | Lung small cell carcinoma | Chemotherapy |
| 71 | 4.86 | Metastacized breast adenocarcinoma | Radiation, hormonal therapy |
| 72 | 5.77 | Adenocarcinoma of the larynx | Chemotherapy |
| 73 | 5.35 | Colon adenocarcinoma | Chemotherapy |
| 74 | 3.71 | Lung adenocarcinoma | Brain meta-radiotherapy |
| 75 | 6.71 | Testicular cancer | Chemotherapy |
| 76 | 19.24 | Cancer of the connective tissue | Surgery |
| 77 | 9.03 | Lung adenocarcinoma | Radiation |
| 78 | 5.45 | Lung small cell carcinoma | Radiation, chemotherapy |
| 79 | 23.93 | Lung adenocarcinoma | None (pleural effusion in lung) |
| 80 | 2.33 | Testicular cancer | Radiation |
| 81 | 13.49 | Lung small cell carcinoma | Hormonal therapy |
| 82 | 12.11 | Rectosigmoidal adenocarcinoma | Radiation |
| 83 | 3.81 | Rectal adenocarcinoma | Chemotherapy |
| 84 | 3.01 | Lung adenocarcinoma | chemotherapy |
| 85 | 2.52 | Adenocarcinoma of the nasopharynx | Radiation |
| 86 | 3.46 | Cancer of the trachea | Radiation |
| 87 | 6.28 | Lung small cell carcinoma | Radiation |
| 88 | 11.82 | Lung small cell carcinoma | Surgery |
| 89 | 9.07 | Bladder carcinoma | Chemotherapy |
| 90 | 3.40 | Prostate adenocarcinoma | Chemotherapy |
| 91 | 3.06 | Colon adenocarcinoma | Surgery |
| 92 | 0.53 | Rectosigmoidal adenocarcinoma | Surgery |
| 93 | 5.62 | Rectal adenocarcinoma | Chemotherapy |
| 94 | 0.64 | Kaposi's sarcoma | Radiation, chemotherapy |
| 95 | 40.80 | Lymphoma | Chemotherapy |
| 96 | 25.38 | Testicular cancer | Radiation |
| 97 | 22.96 | Lung small cell carcinoma | Chemotherapy |
| 96 | 41.37 | Colon adenocarcinoma | Chemotherapy |
| 99 | 26.33 | Malignant melanoma | Metastatic disease |
| 100 | 59.66 | Kidney adenocarcinoma | Surgery |
| 101 | 65.29 | Liver and bile duct adenocarcinoma | Chemotherapy |
| 102 | 12.18 | Lung adenocarcinoma | Surgery, Chemotherapy |
| 103 | 14.89 | Testicular cancer | Surgery |
| 104 | 19.44 | Malignant melanoma | Surgery |
| 105 | 10.48 | Lung small cell carcinoma | Surgery |

EXAMPLE 4

The procedure of Example 1 was repeated except that the formic acid:nicotinic acid ratio was determined from whole blood instead of hemolysed blood. This was done simply by placing blood (without any pretreatment) into a calibrated CS isotachophoteric analyzer EA 100. The procedure was repeated for volunteers 106–118.

Volunteers 106, 108, 109, 111, and 116–118 had formic acid to nicotinic acid ratios that were higher than about 2.2 which indicated that there was a sufficiently high probability that the volunteers had a cancerous or a pre-cancerous condition to warrant further medical investigation. Volunteers 112–115 had formic acid to nicotinic acid ratios that were lower than about 2.2 which indicated that the volunteers did not have a cancerous or pre-cancerous condition.

55% of the volunteers independently verified as having a cancerous or a pre-cancerous condition had a formic acid to nicotinic acid ratio greater than about 2.2 using blood.

Table 5 indicates the formic acid:nicotinic acid ratios of the volunteer as well as the corresponding independent diagnoses.

TABLE 5

| VOLUNTEER | FORMIC ACID: NICOTINIC ACID | INDEPENDENT DIAGNOSIS |
|---|---|---|
| 106 | 32.36 | Pre-carcinoma of the colon |
| 107 | N/A* | Collapse of myocardium |
| 108 | 7.04 | Elevated PSA count (a prostrate pre-cancerous condition) |
| 109 | 3.23 | Carcinoma digestive tract |
| 110 | N/A* | Chronic bacterial lung infection (pre-cancerous condition) |
| 111 | 1.98 | Insufficient lymphocytes, interleukins, depressed immune system (pre-cancerous condition) |
| 112 | 1.35 | healthy |
| 113 | 1.25 | healthy |
| 114 | 1.3 | healthy |
| 115 | 1.28 | healthy |
| 116 | 7.04 | Neuro vegetative syndrome |
| 117 | 13.33 | Chronic inflammation of the uterus (pre-cancerous condition) |
| 118 | 4.65 | Brain tumor |

*no detectable nicotinic acid

What is claimed is:

1. A method for determining whether a mammal warrants medical investigation for a cancerous or a pre-cancerous condition by performing a blood test comprising the steps of (a) obtaining a sample of blood from the mammal; (b) measuring the amount of formic acid in the sample, (c) measuring the amount of nicotinic acid in the sample, and (d) calculating the formic acid to nicotinic acid ratio of the sample, and (e) determining whether the formic acid to nicotinic acid ratio is sufficiently high to warrant medical investigation, wherein a ratio of at least 2.2 warrants medical investigation.

2. The method of claim 1, wherein the formic acid to nicotinic acid ratio is at least 2.7 and medical investigation is warranted.

3. The method of claim 1, wherein the formic acid to nicotinic acid ratio is about 1.8 and lower and no medical investigation is warranted.

4. The method of claim 1, wherein the formic acid to nicotinic acid ratio is at about 2.0 and below and no medical investigation is warranted.

5. The method of claim 1, wherein the cancerous condition is selected from the group of carcinomas, sarcomas, myelomas, lymphomas, and leukemias.

6. The method of claim 1, wherein the cancerous condition is selected from the group of adenocarcinoma of the larynx, adenocarcinoma of the nasopharynx, bladder carcinoma, brain cancer, breast adenocarcinoma, cancer of the connective tissue, cancer of the parotid gland, cancer of the trachea, carcinoma digestive tract, colon adenocarcinoma, gall bladder adecarcinoma, Hodgkin's disease, kidney adenocarcinoma, liver and bile duct adenocarcinoma, lung adenocarcinoma, lung small cell carcinoma, malignant melanoma, metastacized breast adenocarcinoma, rectal adenocarcinoma, prostate adenocarcinoma, rectosigmoidal adenocarcinoma, sarcoma, skin cancer, stomach adenocarcinoma, testicular cancer, rectal adenocarcinoma, Kaposi's sarcoma, lymphoma, leukemia, and multiple myeloma.

7. The method of claim 1, wherein the amount of the formic acid is measured by (a) calibrating an analyzer based upon a sample containing a known amount of formic acid, (b) preparing a hemolyzate from the sample of blood, (c) introducing the hemolyzate into the analyzer, and (d) determining the formic acid content in the hemolyzate.

8. The method of claim 7, wherein the analyzer is selected from the group of capillary electrophoresis, capillary isotachophoresis and capillary chromatography analyzers.

9. The method of claim 1, wherein the amount of the nicotinic acid is measured by (a) calibrating an analyzer based upon a sample containing a known amount of nicotinic acid, (b) preparing a hemolyzate of the sample of blood, (c) introducing the hemolyzate into the analyzer, and (d) determining the nicotinic acid content of the hemolyzate.

10. The method of claim 9, wherein the hemolyzate is deproteinized by adding acetone-water to the hemolyzate prior to introduction of the hemolyzate into the analyzer.

11. A method for determining whether a mammal warrants medical investigation for a cancerous or a pre-cancerous condition by performing a blood test comprising the steps of (a) obtaining a sample of blood from the mammal; (b) measuring the amount of formic acid in the sample, (c) measuring the amount of nicotinic acid in the sample, and (d) calculating the formic acid to nicotinic acid ratio of the sample, and (e) determining whether the formic acid to nicotinic acid ratio is sufficiently high to warrant medical investigation, wherein a ratio of about 1.8 and lower does not warrant medical investigation.

12. The method of claim 11, wherein the amount of the formic acid is measured by (a) calibrating an analyzer based upon a sample containing a known amount of formic acid, (b) preparing a hemolyzate from the sample of blood, (c) introducing the hemolyzate into the analyzer, and (d) determining the formic acid content in the hemolyzate.

13. The method of claim 12, wherein the amount of the nicotinic acid is measured by (a) calibrating an analyzer based upon a sample containing a known amount of nicotinic acid, (b) preparing a hemolyzate of the sample of blood, (c) introducing the hemolyzate into the analyzer, and (d) determining the nicotinic acid content of the hemolyzate.

14. The method of claim 13, wherein the hemolyzate is deproteinized by adding acetone-water to the hemolyzate prior to introduction of the hemolyzate into the analyzer.

* * * * *